(12) United States Patent
Sagel et al.

(10) Patent No.: US 7,122,199 B2
(45) Date of Patent: *Oct. 17, 2006

(54) METHODS FOR WHITENING TEETH

(75) Inventors: Paul Albert Sagel, Mason, OH (US); Robert Stanley Dirksing, Northbend, OH (US); Frederick James Rohman, Loveland, OH (US); Lisa Rae Glaser, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/099,738

(22) Filed: Apr. 6, 2005

(65) Prior Publication Data

US 2005/0196352 A1     Sep. 8, 2005

Related U.S. Application Data

(63) Continuation of application No. 10/321,252, filed on Dec. 17, 2002, now Pat. No. 6,884,426, which is a continuation of application No. 09/864,640, filed on May 24, 2001, now abandoned, which is a continuation of application No. 09/268,185, filed on Mar. 15, 1999, now abandoned, which is a continuation-in-part of application No. 09/040,000, filed on Mar. 17, 1998, now Pat. No. 5,891,453, which is a continuation-in-part of application No. 08/870,330, filed on Jun. 6, 1997, now Pat. No. 5,879,691.

(51) Int. Cl.
*A61K 8/02* (2006.01)

(52) U.S. Cl. ............... 424/401; 424/49; 424/53

(58) Field of Classification Search ........ 424/401, 424/49, 53
See application file for complete search history.

(56) References Cited

U.S. PATENT DOCUMENTS

| | | |
|---|---|---|
| 2,835,628 A | 5/1958 | Saffir |
| 3,070,102 A | 12/1962 | MacDonald |
| 3,625,215 A | 12/1971 | Quisling |
| 3,657,413 A | 4/1972 | Rosenthal et al. |
| 3,688,406 A | 9/1972 | Porter et al. |
| 3,754,332 A | 8/1973 | Warren, Jr. |
| 3,844,266 A | 10/1974 | Cowen |
| 3,902,509 A | 9/1975 | Tundermann et al. |
| 3,955,281 A | 5/1976 | Weitzman |
| 3,972,995 A | 8/1976 | Tsuk et al. |
| 4,138,314 A | 2/1979 | Patil et al. |
| 4,138,814 A | 2/1979 | Weitzman |
| 4,182,222 A | 1/1980 | Stahl |
| 4,211,330 A | 7/1980 | Strock |
| 4,307,075 A | 12/1981 | Martin |
| 4,324,547 A | 4/1982 | Arcan et al. |
| 4,335,731 A | 6/1982 | Bora, Jr. |
| 4,363,843 A | 12/1982 | Crofts |
| 4,376,628 A | 3/1983 | Aardse |
| 4,428,373 A | 1/1984 | Seid et al. |
| 4,431,631 A | 2/1984 | Clipper et al. |
| 4,518,721 A | 5/1985 | Dhabhar et al. |
| 4,522,805 A | 6/1985 | Gordon |
| 4,522,806 A | 6/1985 | Muhlemann et al. |
| 4,528,180 A | 7/1985 | Schaeffer |
| 4,537,778 A | 8/1985 | Clipper et al. |
| 4,544,354 A | 10/1985 | Gores et al. |
| 4,554,154 A * | 11/1985 | White .................. 424/435 |
| 4,557,692 A | 12/1985 | Chorbajian |
| 4,560,351 A | 12/1985 | Osborne |
| 4,568,536 A | 2/1986 | Kronenthal et al. |
| 4,592,487 A | 6/1986 | Simon et al. |
| 4,592,488 A | 6/1986 | Simon et al. |
| 4,661,070 A | 4/1987 | Friedman |
| 4,687,663 A | 8/1987 | Schaeffer |
| 4,696,757 A | 9/1987 | Blank et al. |
| 4,713,243 A | 12/1987 | Schiraldi et al. |
| 4,728,291 A | 3/1988 | Golub |
| 4,741,700 A | 5/1988 | Barabe |
| 4,741,941 A | 5/1988 | Englebert et al. |
| 4,755,385 A | 7/1988 | Etienne et al. |
| 4,755,386 A | 7/1988 | Hsiao et al. |
| 4,765,983 A | 8/1988 | Takayanagi et al. |
| 4,770,634 A | 9/1988 | Pellico |
| 4,786,253 A | 11/1988 | Morais |
| 4,788,052 A | 11/1988 | Ng et al. |
| 4,799,888 A | 1/1989 | Golub |
| 4,812,308 A | 3/1989 | Winston et al. |
| 4,839,156 A | 6/1989 | Ng et al. |
| 4,839,157 A | 6/1989 | Mei-KingNg et al. |
| 4,849,213 A | 7/1989 | Schaeffer |
| RE33,093 E | 10/1989 | Yanagibashi et al. |
| 4,895,721 A | 1/1990 | Drucker |

(Continued)

FOREIGN PATENT DOCUMENTS

CA    1209761    8/1986

(Continued)

OTHER PUBLICATIONS

3M Dental Products 2000 Product Catalog, 32 pages.

(Continued)

*Primary Examiner*—Ralph Gitomer
(74) *Attorney, Agent, or Firm*—Angela K. Haughey; James C. Vago

(57) ABSTRACT

A method of bleaching a plurality of adjacent teeth is disclosed. The teeth having facial and lingual surfaces. The method includes applying a tooth bleaching delivery system to a plurality of adjacent teeth, wherein the tooth bleaching delivery system includes a strip of material and a tooth bleaching composition having a peroxide active.

31 Claims, 3 Drawing Sheets

U.S. PATENT DOCUMENTS

| | | | |
|---|---|---|---|
| 4,900,552 A | 2/1990 | Sanvordeker et al. |
| 4,900,554 A | 2/1990 | Yanagibashi et al. |
| 4,902,227 A | 2/1990 | Smith |
| 4,919,615 A | 4/1990 | Croll |
| 4,968,251 A | 11/1990 | Darnell |
| 4,971,782 A | 11/1990 | Rudy et al. |
| 4,972,946 A | 11/1990 | Whittaker |
| 4,980,152 A | 12/1990 | Frazier et al. |
| 4,983,379 A | 1/1991 | Schaeffer |
| 4,983,381 A | 1/1991 | Zaragoza |
| 4,988,500 A | 1/1991 | Hunter et al. |
| 4,990,089 A | 2/1991 | Munro |
| 5,059,417 A | 10/1991 | Williams et al. |
| 5,076,791 A | 12/1991 | Madray, Jr. |
| 5,084,268 A | 1/1992 | Thaler |
| 5,098,303 A | 3/1992 | Fischer |
| 5,122,365 A | 6/1992 | Murayama |
| 5,165,424 A | 11/1992 | Silverman |
| 5,166,233 A | 11/1992 | Kuroya et al. |
| RE34,196 E | 3/1993 | Munro |
| 5,211,559 A | 5/1993 | Hart et al. |
| 5,234,342 A | 8/1993 | Fischer |
| 5,256,402 A | 10/1993 | Prencipe et al. |
| 5,290,566 A | 3/1994 | Schow et al. |
| 5,310,563 A * | 5/1994 | Curtis et al. ............. 424/616 |
| 5,326,685 A | 7/1994 | Gaglio et al. |
| 5,332,576 A | 7/1994 | Mantelle |
| 5,340,314 A | 8/1994 | Tarvis |
| 5,340,581 A | 8/1994 | Tseng et al. |
| 5,356,291 A | 10/1994 | Darnell |
| 5,376,006 A | 12/1994 | Fischer |
| 5,380,198 A | 1/1995 | Suhonen |
| 5,401,495 A | 3/1995 | Murayama |
| 5,409,631 A | 4/1995 | Fischer |
| 5,425,953 A | 6/1995 | Sintov et al. |
| 5,438,076 A | 8/1995 | Friedman et al. |
| 5,472,704 A | 12/1995 | Santus et al. |
| 5,505,933 A | 4/1996 | Norfleet et al. |
| 5,522,726 A | 6/1996 | Hodosh |
| 5,560,379 A | 10/1996 | Pieczenik |
| 5,565,190 A | 10/1996 | Santalucia et al. |
| 5,575,654 A | 11/1996 | Fontenot |
| 5,575,655 A | 11/1996 | Darnell |
| 5,599,553 A | 2/1997 | Chung |
| 5,611,687 A | 3/1997 | Wagner |
| 5,620,322 A | 4/1997 | Lococo |
| 5,626,866 A | 5/1997 | Ebert et al. |
| 5,631,000 A | 5/1997 | Pellico et al. |
| 5,639,445 A | 6/1997 | Curtis et al. |
| 5,662,758 A | 9/1997 | Hamilton et al. |
| 5,678,273 A | 10/1997 | Porcelli |
| 5,700,478 A | 12/1997 | Biegajski et al. |
| 5,707,235 A | 1/1998 | Knutson |
| 5,707,736 A | 1/1998 | Levy et al. |
| 5,713,738 A | 2/1998 | Yarborough |
| 5,723,132 A | 3/1998 | Tseng et al. |
| 5,725,843 A | 3/1998 | Fischer |
| 5,746,598 A | 5/1998 | Fischer |
| 5,759,037 A | 6/1998 | Fischer |
| 5,759,038 A | 6/1998 | Fischer |
| 5,770,105 A | 6/1998 | Fischer |
| 5,770,182 A | 6/1998 | Fischer |
| 5,780,045 A | 7/1998 | McQuinn et al. |
| 5,819,765 A | 10/1998 | Mittiga |
| 5,827,591 A | 10/1998 | Blok et al. |
| 5,846,058 A | 12/1998 | Fischer |
| 5,851,512 A | 12/1998 | Fischer |
| 5,855,870 A | 1/1999 | Fischer |
| 5,858,332 A | 1/1999 | Jensen et al. |
| 5,879,691 A * | 3/1999 | Sagel et al. ............. 424/401 |
| 5,891,453 A * | 4/1999 | Sagel et al. ............. 424/401 |
| 5,894,017 A | 4/1999 | Sagel et al. |
| 5,922,307 A | 7/1999 | Montgomery |
| 5,953,885 A | 9/1999 | Berman et al. |
| 5,968,633 A | 10/1999 | Hamilton et al. |
| 5,980,249 A | 11/1999 | Fontenot |
| 5,985,249 A | 11/1999 | Fischer |
| 5,989,569 A | 11/1999 | Dirksing et al. |
| 6,036,943 A | 3/2000 | Fischer |
| 6,045,811 A | 4/2000 | Dirksing et al. |
| 6,094,889 A | 8/2000 | VanLoon et al. |
| 6,096,328 A | 8/2000 | Sagel et al. |
| 6,136,297 A | 10/2000 | Sagel et al. |
| 6,182,420 B1 | 2/2001 | Berman et al. |
| 6,197,331 B1 | 3/2001 | Lerner et al. |
| 6,277,458 B1 | 8/2001 | Dirksing et al. |
| 6,309,625 B1 | 10/2001 | Jensen et al. |
| 6,322,360 B1 | 11/2001 | Burgio |
| 6,461,158 B1 | 10/2002 | Sagel et al. |
| 6,551,579 B1 | 4/2003 | Sagel et al. |
| 6,582,708 B1 | 6/2003 | Sagel et al. |
| 6,884,426 B1 * | 4/2005 | Sagel et al. ............. 424/401 |
| 6,949,240 B1 * | 9/2005 | Sagel et al. ............. 424/53 |

FOREIGN PATENT DOCUMENTS

| | | |
|---|---|---|
| CA | 2078980 | 10/1993 |
| CA | 2095445 | 7/1995 |
| CA | 2000040 | 10/1995 |
| CA | 2162536 | 5/1996 |
| CA | 2162812 | 5/1996 |
| CA | 2162885 | 5/1996 |
| DE | 1104116 | 4/1961 |
| DE | 2330869 | 1/1975 |
| EP | 0 063 604 | 4/1982 |
| EP | 0 200 508 | 12/1986 |
| EP | 0 252 459 | 1/1988 |
| EP | 0 381 194 | 8/1990 |
| EP | 0569797 A2 | 11/1993 |
| EP | 0636378 A1 | 2/1995 |
| EP | 0763358 | 9/1996 |
| FR | 2637 175 A | 4/1990 |
| FR | 2701397 A1 | 8/1994 |
| GB | 1142325 | 2/1969 |
| GB | 1240411 | 7/1971 |
| GB | 2108841 | 5/1983 |
| GB | 2159052 | 11/1985 |
| JP | 60005159 | 1/1985 |
| JP | 60005160 | 1/1985 |
| JP | 63005756 | 1/1988 |
| JP | 6354318 | 3/1988 |
| JP | 1-279838 | 11/1989 |
| JP | 2250826 | 10/1990 |
| JP | 3-264522 | 11/1991 |
| JP | 3-264523 | 11/1991 |
| JP | 08325128 A2 | 12/1996 |
| JP | 10-17448 | 1/1998 |
| RU | 2075965 | 9/1994 |
| WO | WO 88/06879 | 9/1988 |
| WO | WO 89/10740 | 11/1989 |
| WO | WO 91/03236 | 3/1991 |
| WO | WO 93/01790 | 2/1993 |
| WO | WO 95/05416 | 2/1995 |
| WO | WO 95/17158 | 6/1995 |
| WO | WO 95/24872 | 9/1995 |
| WO | WO 97/25968 | 7/1996 |
| WO | WO 96/25910 | 8/1996 |
| WO | WO 98/17263 | 4/1998 |
| WO | WO 99/62472 * | 12/1999 |
| WO | WO 00/044845 | 8/2000 |
| WO | WO 00/54699 * | 9/2000 |
| WO | WO 01/001958 | 1/2001 |

| WO | WO 01/030263 | 5/2001 |

OTHER PUBLICATIONS

Besner, E., et al., Practical Endodontics, 1994, pp. 7-15, 178-180; Mosby-Year Book, Inc.

S.M. Newman, et al., "Tray-Forming Technique for Dentist-Supervised Home Bleaching", *Quintessence International*, 1995, pp. 447-453, vol. 26, No. 7.

G. McLaughlin, et al., "Materials" and "Clinical Techniques", *Color Atlas of Tooth Whitening*, 1991, pp. 35-38 & 45-50, Ishiyaku EuroAmerica, Inc.

R.E. Goldstein, et al., "Chemistry of Bleaching", *Complete Dental Bleaching*, 1995, pp. 25-32 & 90-97, Quintessence Publishing Co, Inc.

V.B. Haywood, et al., "Nightguard Vital Bleaching", *Quintessence International*, 1989, vol. 20, No. 3, pp. 173-176, 19th International Meeting on Dental Implants and Transplants, Bologna, Italy.

V.B. Haywood, "History, Safety, and Effectiveness of Current Bleaching Techniques and Applications of the Nightgaurd Vital Bleaching Technique", *Quintessence International*, 1992, vol. 23, No. 7, pp. 471-488.

V.B. Haywood, "Nightguard Vital Bleaching", *Dentistry Today*, 1997, pp. 86-91.

"Tooth Bleaching, Home-Use Products", *Clinical Research Associates Newsletter*, 1989, vol. 3, Issue 12.

Ralph H. Leonard Jr., et al, "Risk factors for developing tooth sensitivity and gingival irritation associated with nightguard vital bleaching", *Esthetic Dentristy*, 1997, vol. 28, No. 8, pp. 527-534.

Van B. Haywood, et al, "Nightguard vital bleaching: how safe is it?", *Esthetic Dentistry*, 1991, vol. 22, No. 7, pp. 515-523.

Van B. Haywood, "History, safety and effectiveness of current bleaching techniques and applications of the nightguard vital bleaching technique", *Esthetic Dentistry*, 1992, vol. 23, No. 7, pp. 471-488.

Van B. Haywood, "Bleaching of vital and notvital teeth", *Periodontology and Restorative Dentistry*, 1992, pp. 142-149.

Van B. Haywood, "Nightquard vital bleaching , a history and products update: Part 1", *Esthestic Dentistry Update*, 1991, vol. 2, No. 4, pp. 63-66.

Van B. Haywood, "Nightguard vital bleaching, a history and products update: Part 2", *Esthestic Dentistry Update*, 1991, vol. 2, No. 5, pp. 82-85.

Claudia Paula Drew, "Teeth Bleaching . . . a Vital technique for you to know", 1988, Sep./Oct., pp. 23-25.

Van Benjamin Haywood, "Overview and Status of Mouthguard Bleaching" *Journal of Esthetic Dentistry*, 1991, vol. 3, No. 5, pp. 157-161.

Van B. Haywood, "Nightguard vital bleaching: current information and research", *Esthetic Dentistry Update*, 1990, vol. 1, No. 2, pp. 20-25.

Carolyn F. G. Wilson, et al, "Color change following vital bleaching of tetracycline-stained teeth" *Pediatric Dentistry*, 1985, vol. 7, No. 3, pp. 205-208.

"Tooth Bleaching, Home-Use Products", *Clinical Research Asociates Newsletter*, 1989, pp. 1-4.

Sue Ellen Richardson, "Home bleaching: effectiveness, history, technique, bleaches, cost and safety" *The Journal of the Greater Houston Dental Society*, 1989, pp. 22-26.

Van B. Haywood, "The food and drug administration and its influence on home bleaching", *ADA*, 1993, pp. 12-18.

Van. B. Haywood, "Efficacy of foam liner in 10% carbamide peroxide bleaching technique", *Esthetic Dentistry*, 1993, vol. 24, No. 9, pp. 663-666.

Christopher J. Woolverton, "Toxicity of two carbamide peroxide products used in nightguard vital bleaching", *American Journal of Dentistry*, 1993, vol. 6, No. 6, pp. 310-314.

Van B. Haywood, "Response of normal and tetracycline-stained teeth with pulp-size variation to nightguard vital bleaching", *Journal of Esthetic Dentistry*, 1994, vol. 6, No. 3, pp. 109-114.

Ralph H. Leonard, et al, "Salivary pH changes during 10% carbamide peroxide bleaching" *Dental Research*, 1994, vol. 25, No. 8, pp. 547-550.

Ralph H. Leonard, et al, "Change in pH of plaque and 10% carbamide peroxide solution during nightguard vial bleaching treatment" *Esthetic Dentistry*, 1994, vol. 25, No. 12, pp. 819-823.

Van B. Haywood, "Historical development of whiteners: clinical safety and efficacy", *Aesthetics*, 1997, pp. 98-104.

Van B. Haywood, "Considerations and variations of dentist-prescribed, home-applied vital tooth-bleaching techniques", *Compend Contin Educ Dent*, 1994, Suppl. No. 17, pp. s616-s621.

Van B. Haywood, "Effectiveness, side effects and long-term status of nightguard vital bleaching", *JADA*, 1994, vol. 125, pp. 1219-1226.

James W. Curtis, et al, "Assessing the effects of 10 percent carbamide peroxide on oral soft tissues", *JADA*, 1996, vol. 127, pp. 1218-1223.

Fonda G. Robinson, et al, "Effect of 10 percent carbamide peroxide on color of provisional restoration materials", *JADA*, 1997, vol. 128, pp. 727-731.

Van B. Haywood, "Commonly asked questions about nightguard vital bleaching", *IDA Journal*, 1993, pp. 28-33.

Van B. Haywood, "Nightguard Vital Bleaching", *Dentistry Today*, 1997, pp. 88-91.

Van B. Haywood, "Nightguard vital bleaching: current concepts and research", *JADA*, 1997, vol. 128, pp. 19s-25s.

Van B. Haywood, "Commonly asked questions about nightguard vital bleaching", *The Dental Assistant*, Mar./Apr. 1996, pp. 6-12.

M.S. McCracken, "Demineralization effects of 10 percent carbamide peroxide", *Journal of Dentistry*, 1996, vol. 24, No. 6, pp. 395-398.

Messing, J.J., et al., *Color Atlas of Endodontics*, 1988, pp. 106-107, 135-140, 173-175, 257-259; The C.V. Mosby Company, Ltd.

Van B. Haywood, "Efficacy of six months of nightguard vital bleaching of tetracycline-stained teeth", *Journal of Esthetic Dentistry*, 1997, vol. 9, No. 1, pp. 13-19.

Van B. Haywood, "Achieving, maintaining and recovering successful tooth bleaching", *Journal of Esthetic Dentistry*, 1996, vol. 8, No. 1, pp. 31-38.

Carl M. Russell, et al, "Dentist-supervised home bleaching with ten percent carbamide peroxide gel: a six month study", *Journal of Esthetic Dentistry*, 1996, vol. 8, No. 4, pp. 177-182.

Van B. Haywood, "Historical development of whiteners: clinical safety and efficacy", *Aesthetics*, 1997 April update, pp. 98-104.

Office Action from the United States Patent & Trademark Office, dated Sep. 5, 2003, issued on U.S. Appl. No. 09/864,686, filed May 24, 2001, assignee—The Procter & Gamble Company, now abandoned.

Office Action from the United States Patent & Trademark Office, dated May 28, 2003, issued on U.S. Appl. No. 09/864,686, filed May 24, 2001, assignee—The Procter & Gamble Company, now abandoned.

\* cited by examiner

METHODS FOR WHITENING TEETH

This is a continuation of application Ser. No. 10/321,252, filed Dec. 17, 2002, now U.S. Pat. No. 6,884,426 which is a continuation of Ser. No. 09/864,640, filed May 24, 2001, now abandoned which is a continuation of application Ser. No. 09/268,185, filed Mar. 15, 1999 now abandoned, which is a continuation-in-part of application Ser. No. 09/040,000, filed Mar. 17, 1998, now U.S. Pat. No. 5,891,453, which is a continuation-in-part of application Ser. No. 08/870,330, filed Jun. 6, 1997, now U.S. Pat. No. 5,879,691, the substances of which are incorporated herein by reference.

FIELD OF THE INVENTION

The present invention relates to methods for whitening teeth, and more particularly, to methods for whitening teeth using a strip of material and a tooth whitening substance.

BACKGROUND OF THE INVENTION

Tooth whitening has become popular in today's culture. More and more consumers are searching for the best method to achieve tooth whitening. Professional tooth bleach by a dentist is common. Generally, there are two types of professional tooth bleaching: in the dentist's office or outside of the dentist's office. In the office tooth bleaching generally involves several visits to the dentist and the use of a rubber dam to protect the patient's gums from the bleaching agents. Out of the office tooth bleaching generally involves the use of a device or tray which is made in the dental office to fit the patient's teeth. The device is reused, and therefore, must be sufficiently robust to endure repeat handling, cleaning, filling, installation, and wearing. Typically, a patient uses the device in time periods when social contact can be avoided.

There are now non-professional programs available to persons interested in whitening their teeth using commercial products available at drug stores. The commercial products provide a kit which includes a generic appliance and a container of bleaching gel. The obvious appeal is the lower cost of the program. A major disadvantage of this generic "one size fits all" appliance is the greater void space between the interior walls of the appliance and the teeth versus a professionally fitted appliance. Hence, in order to insure intimate contact of the bleaching gel and the teeth surfaces, more bleaching gel is required. Furthermore, the poorer fit means a greater loss of bleaching gel onto the gums, into the oral cavity, and eventual ingestion. The commercial kits, an the outside-the-office professionally administered program, require the user to clean and to reuse the appliance. Since generic appliances are not fitted to the individual user, they are even more bulky in the mouth than the fitted appliances and thus they restrict social discourse to a greater degree.

One attempt to remedy some of the problems of the commercial kits is disclosed in U.S. Pat. No. 5,575,654, issued to Fontenot on Nov. 19, 1996. Fontenot discloses a prepackaged moldable dental appliance adapted to fit a wide range of variously sized dental arches. In use, the dental appliance is removed from the packaging, aligned in a parallel fashion to the edges of the teeth and pushed over the teeth in the direction of the periodontal tissue until it covers the teeth surfaces.

Another solution is disclosed in U.S. Pat. No. 5,310,563, issued to Curtis et al. on May 10, 1994. Curtis et al. disclose a putty-like material which is formed by pressing against the teeth. It is held in place by mechanical engagement with undercut surfaces and by friction. The composition encapsulates the active.

Other methods are disclosed in U.S. Pat. No. 5,425,953, issued to Sintov et al. on Jun. 20, 1995. Sintov et al. discloses a liquid polymer composition for bleaching of the teeth. The liquid polymer composition forms a film after applied to the teeth. Other references which disclose using a film in the oral cavity include U.S. Pat. No. 4,713,243 issued to Schiraldi et al. on Dec. 15, 1987, and U.S. Pat. No. 2,835,628, issued to Saffir on May 20, 1958.

SUMMARY OF THE INVENTION

A method of bleaching a plurality of adjacent teeth is disclosed. The teeth having facial and lingual surfaces. The method includes applying a tooth bleaching delivery system to a plurality of adjacent teeth, wherein the tooth bleaching delivery system includes a strip of material and a tooth bleaching composition having a peroxide active.

BRIEF DESCRIPTION OF THE DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

DETAILED DESCRIPTION OF THE INVENTION

The abbreviation "cm", as used herein, means centimeter. The abbreviation "mm", as used herein, means millimeter.

Figure 1:
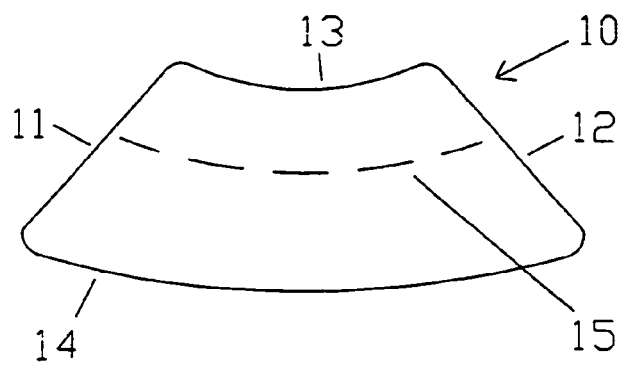
FIG. 1 is a planar view of a tooth whitening strip of material which is substantially trapezoidal in shape.

Referring now to the drawings, and more particularly to FIG. 1, there is shown a first preferred embodiment of the present invention, which is generally indicated as 10. Embodiment 10 represents a tooth whitening strip which is substantially trapezoidal in shape. Embodiment 10 has a first side 11 and second side 12, a third side 13, and a fourth side 14. First side 11 and second side 12 are straight sides which angle in from the fourth side 14 to the third side 13. Third side 13 is concave and shorter then the fourth side 14. The fourth side 14 is convex. The fourth side 14 will be placed close to the bottom edge of the front side of a user's bottom set of front teeth. Alternatively, if the strip is worn on the user's top set of teeth, the fourth side 14 may be placed along the top part of the front side of a user's top set of front teeth. A fold line 15 of embodiment 10 extends from first side 11 to second side 12. The fold line 15 may be located closer to the third side 13 or the fourth side 14. The fold line 15 will be determined by the size of the user's teeth and the placement of the tooth whitening strip on the user's teeth. The third side 13 will be along the back side of a user's teeth after the strip 10 is folded along the fold line 15.

Figure 2:
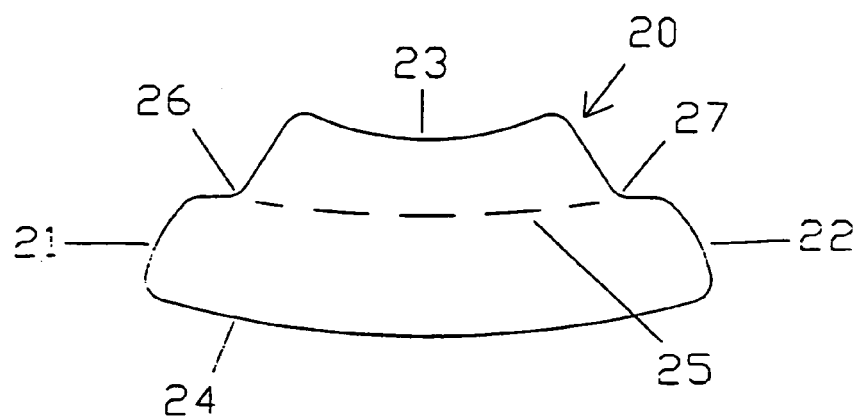
FIG. 2 is a planar view of a tooth whitening strip which is substantially trapezoidal in shape with stair stepped sides.

As shown in FIG. 2 by embodiment 20, the tooth whitening strip of material may be substantially trapezoidal in shape with stair stepped sides. Embodiment 20 has a first side 21, a second side 22, a third side 23, and a fourth side 24. Third side 23 is concave and shorter then the fourth side 24. The fourth side 24 is convex. First side 21 and second side 22 are both stair step sides. Fold line 15 extends from the corners 26 and 27 of the stair step in the first side 21 and the second side 22, respectively. Embodiment 20 can alternatively be described as two substantially trapezoidal shapes placed on top of one another. The top trapezoid is formed by the third side 23, the second side 22 from its corner 27 up to the third side 23, the fold line 25, and the first side 21 from its corner 26 up to the third side 23. The bottom trapezoid is formed by the fold line 25, the second side 22 from its corner 27 down to the fourth side 24, the fourth side 24, and the first side 21 from its corner 26 down to the fourth side 24.

Figure 3:
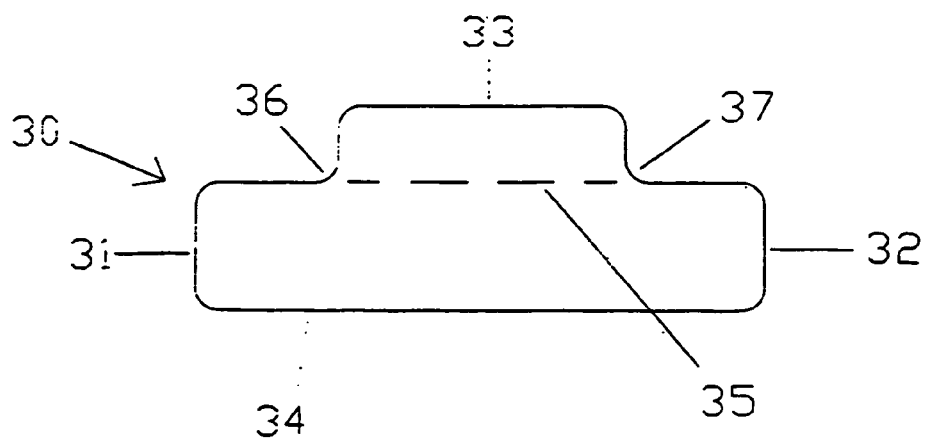
FIG. 3 is a planar view of a tooth whitening strip which is substantially rectangular in shape with stair stepped sides.

FIG. 3 illustrates an alternative embodiment 30 of the present invention. The tooth whitening strip of material may be substantially rectangular in shape with stair stepped sides. Embodiment 30 has a first side 31 and second side 32, a third side 33, and a fourth side 34. First side 31 and second side 32 are both stair step sides. Fold line 35 extends from the corners 36 and 37 of the stair step in the first side 31 and the second side 32, respectively. Embodiment 30 can also be described as two rectangles placed on top of one another. The top rectangle is formed by the third side 33, the second side 32 from its corner 37 up to the third side 33, the fold line 35, and the first side 31 from its corner 36 up to the third side 33. This top rectangle may alternatively be described as a flap which fits over the back sides of the user's teeth. The bottom rectangle is formed by the fold line 35, the second side 32 from its corner 37 down to the fourth side 34, the fourth side 34, and the first side 31 from its corner 36 down to the fourth side 34.

The fold line 35 will be placed over the tips of a user's teeth enabling the strip to fold down onto both the front side and the back side of the user's teeth. The strip will be placed so that the user's two canine teeth are just outside of corners 36 and 37. The fourth side 34 will be located close to the bottom edge of the front side of a user's bottom set of front teeth. Alternatively if the strip is worn on the user's top set of teeth, the fourth side 34 may be placed along the top part of the front side of a user's top set of front teeth. The third side 33 will be along the back side of a user's teeth.

Figure 4:
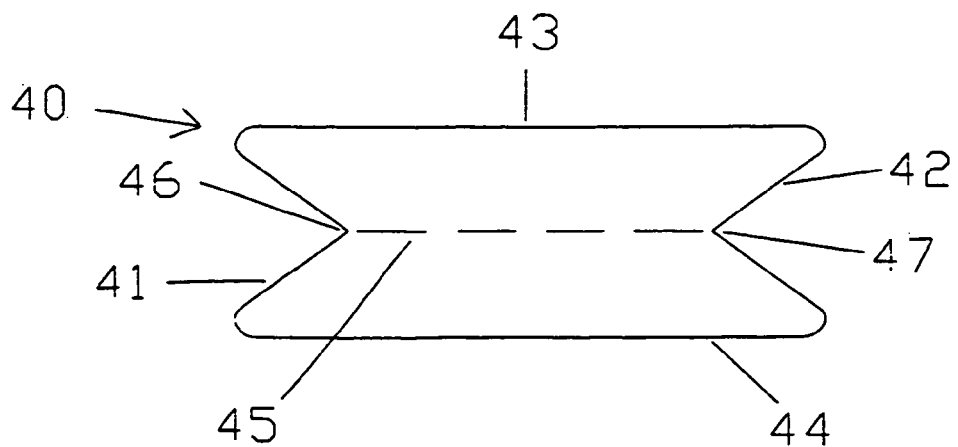
FIG. 4 is a planar view of a tooth whitening strip which is substantially rectangular in shape with notched sides.

FIG. 4 details a tooth whitening strip of material substantially rectangular in shape with notched sides. Embodiment 40 has a first side 41, second side 42, a third side 43, and a fourth side 44. Third side 43 and fourth side 44 are both substantially straight sides and the same length. First side 41 and second side 42 have notches 46 and 47, respectively, which enable the tips of the canine teeth not to be covered when the strip is placed on the user's teeth. Fold line 45 extends from notch 46 in the first side 41 to notch 47 in the second side 42. Notches 46 and 47 as have a sideways V shapes as shown. The notches may be of any shape including rectangular, semi circles, etc. that allows the tips of the canine teeth to not be wrapped by embodiment 40.

Figure 5:
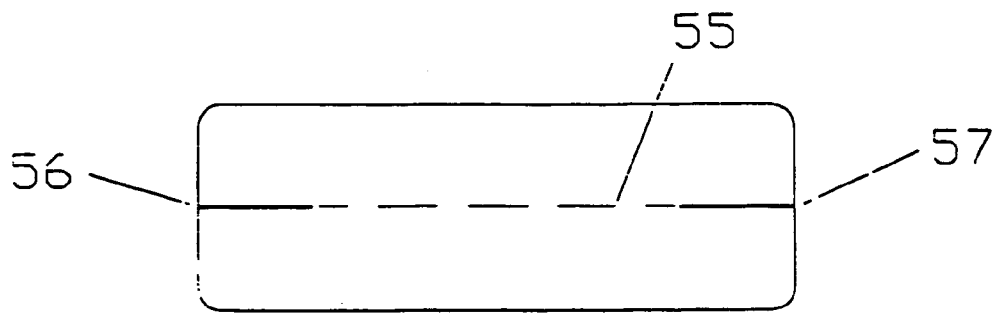
FIG. 5 is a planar view of a tooth whitening strip which is rectangular in shape with two slits.
Figure 6:
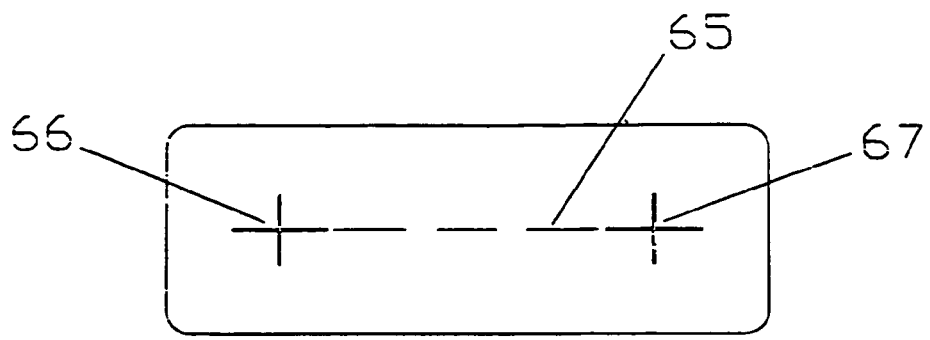
FIG. 6 is a planar view of a tooth whitening strip which is rectangular in shape with two cross-slits.
Figure 7:
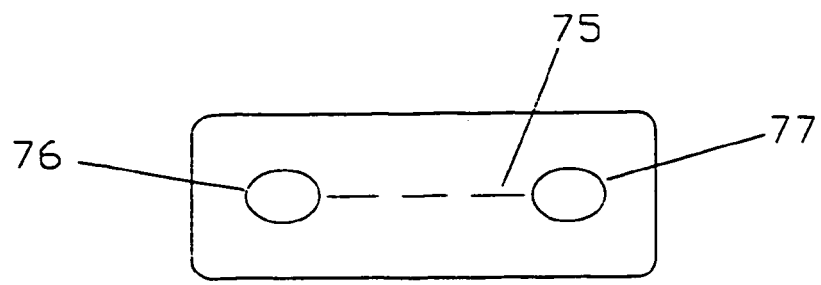
FIG. 7 is a planar view of a tooth whitening strip which is rectangular in shape with two holes.

Embodiments 50, 60, and 70 are illustrated by FIGS. 5, 6, and 7 respectively. The tooth whitening strip of material of embodiments 50, 60, and 70 is substantially rectangular in shape with rounded corners. Each embodiment contains two recesses which allow for protrusion of the canine teeth when the tooth whitening strip is placed on a user's teeth. FIG. 5 illustrates where the recesses are straight slits 56 and 57. Slits 56 and 57 extend from the outside edge of embodiment 50 to an interior point. Fold line 55 extends between slits 56 and 57. FIG. 6 shows slits 66 and 67 which are cross-slits. Cross-slits 66 and 67 are located within embodiment 60. Fold line 65 extends from cross-slit 66 to cross-slit 67. Embodiment 70 of FIG. 7 illustrates holes 76 and 77 in the strip. Holes 76 and 77 may be of any size that is sufficient for the tips of the canines to protrude. Fold line 75 extends between holes 76 and 77.

Figure 8:
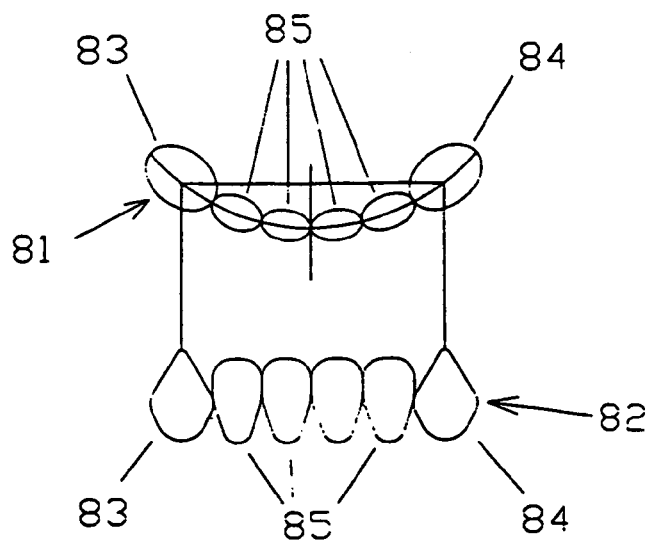
FIG. 8 is a cross-sectional view of a user's front six teeth.

FIG. 8 shows corresponding top 81 and front 82 view of a user's bottom set of the front six teeth. Top view 81 illustrates the general arched shape found in the front six teeth. The two canine teeth 83 and 84 are located on opposite sides of the four front teeth 85. Not shown are additional back teeth, such as molars, which are located next to each of the canine teeth. Front view 82 illustrates the general shapes, including the tips, of the front four teeth 85 and canine teeth 83 and 84.

Figure 9:
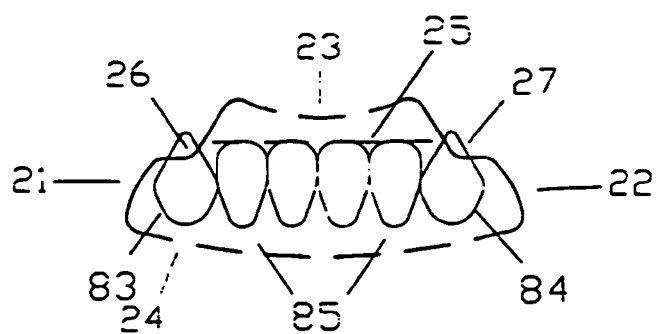
FIG. 9 is cross-sectional view of a tooth whitening strip placed upon a user's front six teeth before being folded over the back sides of the user's teeth.

FIG. 9 shows front view 82 of a user's front six teeth shown in FIG. 8 with the tooth whitening strip illustrated by embodiment 20 of FIG. 2. Embodiment 20 is shown placed along the teeth but not yet folded over the teeth. As illustrated, fourth side 24 is placed along the bottom portions of the front four teeth 85 and the two canine teeth 83 and 84. Fold line 25 hits at the tips of the front four teeth 85 and allows the tips of the canine teeth 83 and 84 to be exposed. Canine teeth 83 and 84 protrude at the corners 26 and 27 of the stair steps. Third side 23 will subsequently be folded down onto the back side of the four front teeth 85.

Tooth Whitening Strip

The tooth whitening strip may be called a tooth whitening strip of material, a strip of material, or a strip. The tooth whitening strip of material will have a shape that is adapted to fit a user's teeth. It is preferred that the strip substantially covers the front side of at least a user's front four teeth and two canine teeth. These teeth are the most visible teeth for most users. The strip of material may cover the front side of additional teeth such as the teeth next two the canine teeth. This may be desired if these teeth are visible to others. By substantially, it is meant that at least half of the front tooth surface is covered. The tooth whitening strip may cover all of the front tooth surface and may also cover portions of the gums adjacent to the teeth. Generally, the tooth whitening strip will begin coverage at the point where the surface of the teeth intersect the gums.

The tooth whitening strip will be foldable over the tips and onto the back sides of one or more of the front four teeth without covering the tips of the two canine teeth. The shape of the strip will allow for canine tips to not be covered. By folding over the tips it is meant that the strip covers or wraps around the front side of the tooth over the tip and onto the back side of the tooth. Depending upon the size of the strip of material, the entire back side of the tooth including the adjacent gum may be covered or only a portion of the back side of the tooth.

The shape of the tooth whitening strip is critical to allow for coverage of the front side of the canines by not coverage of the tips. The shape of the strip may be any shape which allows this to result. The shape of the tooth whitening strip may be of many shapes. The strip may be substantially trapezoidal in shape. The term substantially trapezoidal is used to mean any shape having four general sides where there are two sides which are generally parallel or arched the same way. This may result when one side is convex and the opposing side is concave. The arched shape may help to reduce bunching of the strip and allow the strip to lay smoother along the surfaces of the teeth. The other two opposing sides will generally not be parallel. The strip may be substantially rectangular in shape. This is used generally to mean a shape with four sides which each of two sides are close to parallel. Parallel is used broadly to include when sides are arched, not straight, and generally not perpendicular. Alternatively, the strip may be of any shape such as round or oval. The strip may also be of a shape with many numbers of sides. The shape of the strip does not need to be symmetrical.

Any of the sides or edges of the strip may be notched, stair stepped, or arched. By notched it is meant that there is a recess, indentation, or curve of some type. By stair stepped it is meant that the side is not straight and may contain one or more stair steps. The strip may also contain slits, cross-slits, holes, perforations, or any suitable formation that allows for the canines to protrude through or be avoided by the strip of material. In generally, a recess should allow approximately 2 cm for protrusion of the canines.

Each strip of material will contain a fold line. The fold line is defined as the part of the strip where the tips of the teeth meet the strip when the strip is folded or wrapped over the tips. This line may be from the point where one recesses, stair steps, or notch on one side extends into the strip the farthest to where the other recess, stair step, or notch extends into the strip the farthest on the opposing side. For example, at the corner of a stair step or at the point of a notch. The fold line will generally extend from one side of the strip to another parallel side and along the longer part of the strip. The fold line may be self adjusting depending upon the size and shape of the strip. With a trapezoidal shape strip, the fold line will be determined based upon the positioning of the strip on a user's teeth. The fold line is generally up to about 4 cm in length for a strip designed to fit on a user's bottom set of teeth. There is not a minimum requirement for the fold line as long as part of the strip folds over the tips of at least part of one of the front four teeth. Generally, the fold line will be from about 0.1 cm to about 4 cm, preferably from about 0.5 cm to about 3.5 cm, more preferably from about 1 cm to about 3.2 cm, and most preferably from about 2 cm to about 3.1 cm. For the top set of a user's teeth, the fold line is up to about 4.3 cm in length. The fold line is generally from about 0.1 cm to about 4.3 cm, preferably from about 0.5 cm to about 4 cm, more preferably from about 1 cm to about 3.5 cm and most preferably from about 2 cm to about 3.4 cm.

Preferably, the shape of the strip of material is any shape that has rounded corners. "Rounded corners" is defined as not having any sharp angles or points. The conformable strip of material is preferably of a size that individually fits the row of teeth desired to be bleached. The size of the strip of material depends upon many factors, including the number of teeth to be bleached, the size of the teeth, and personal preference of the wearer. In general, the length of the strip of material is from about 2 cm to about 12 cm, preferably from about 3 cm to about 9 cm, and more preferably from about 4 cm to about 6 cm. If the strip of material is stair stepped on the sides or trapezoidal shaped, the longer side of the strip of material is generally from about 3 cm to about 12 cm, preferably from about 3.1 to about 10 cm, more preferably from about 3.5 cm to about 8 cm, and most preferably from about 4 cm to about 6 cm. The shorter side is from about 0.1 cm to about 12 cm, preferably from about 0.5 cm to about 8 cm, more preferably from about 1 cm to about 5 cm, and most preferably from about 1.5 cm to about 3 cm. The width of the strip of material will also depend upon many factors, including whether or not the strip of material wraps completely around the teeth and covers part or all of the front and back surfaces of the tooth. In a general application, the width of the strip of material is from about 0.5 cm to about 4 cm and preferably from about 1 cm to about 2 cm.

The strip of material serves as a protective barrier to substantially prevent saliva contacting the tooth whitening substance and leaching and/or erosion of the tooth whitening substance from the surface of the teeth by the wearer's lips, tongue, and other soft tissue. In order for an active in tooth whitening substance to act upon the surface of tooth over an extended period of time, from several minutes to several hours, it is important to minimize such leaching and/or erosion. The term "act upon" is herein defined as bringing about a desired change. For example, if the substance is a tooth whitener, it bleaches color bodies to bring about whitening.

The strip of material may comprise materials such as polymers, natural and synthetic wovens, non-wovens, foil, paper, rubber, and combinations thereof. The strip of material may be a single layer of material or a laminate of more than one layer. Generally, the strip of material is substantially water impermeable. The material may be any type of polymer that meets the required flexural rigidity and is compatible with tooth whitening actives, such as peroxide. The material may comprise a single polymer or a mixtures of polymers. Suitable polymers include, but are not limited to, polyethylene, ethylvinylacetate, ethylvinyl alcohol, polyesters such as Mylar® manufactured by DuPont, fluoroplastics such as Teflon® manufactured by DuPont, and combinations thereof. Preferably, the material is polyethylene. The strip of material is generally less than about 1 mm thick, preferably less than about 0.05 mm thick, and more preferably from about 0.001 to about 0.03 mm thick. A polyethylene strip of material is preferably less than about 0.1 mm thick and more preferably from about 0.005 to about 0.02 mm thick.

The strip of material may contain shallow pockets. When the substance is coated on a substance-coated side of strip of material, additional substance fills shallow pockets to provide reservoirs of additional substance. Additionally, the shallow pockets help to provide a texture to the delivery system. The film will preferably have an array of shallow pockets. Generally, the shallow pockets are approximately 0.4 mm across and 0.1 mm deep. When shallow pockets are included in the strip of material and substances are applied to it in various thicknesses, the overall thickness of the delivery system is generally less than about 1 mm. Preferably, the overall thickness is less than about 0.5 mm.

Flexural stiffness is a material property that is a function of a combination of strip thickness, width, and material modulus of elasticity. This test is a method for measuring the rigidity of polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter, wired to the strain gauge is calibrated in grams of deflection force. The rigidity of the sample is read directly from the microammeter and expressed as grams per centimeter of sample strip width. In the present invention, the strip of material has a flexural stiffness of less than about 5 grams/ cm as measured on a Handle-O-Meter, model #211-300, available from Thwing-Albert Instrument Co. of Philadelphia, Pa., as per test method ASTM D2923-95. Preferably, the strip of material has a flexural stiffness less than about 4 grams/cm, more preferably less than about 3 grams/cm, and most preferably from about 0.1 grams/cm to about 1 grams/cm. Preferably, the flexural stiffness of the strip of material is substantially constant and does not significantly change during normal use. For example, the strip of material does not need to be hydrated for the strip to achieve the low flexural stiffness in the above-specified ranges.

This relatively low stiffness enables the strip of material to drape over the contoured surfaces of teeth with very little force being exerted; that is, conformity to the curvature of the wearer's mouth and gaps between adjacent teeth is maintained because there is little residual force within strip of material to cause it to return to its substantially flat shape. The flexibility of the strip enables the strip of material to contact adjoining soft tissue over an extended period of time without physical irritation. The strip of material does not require pressure forming it against the teeth.

The strip of material is held in place on a plurality of adjacent teeth by adhesive attachment provided by the substance. The viscosity and general tackiness of the substance cause the strip of material to be adhesively attached to a plurality of adjacent teeth without substantial slippage under the potential friction from the lips, tongue, and other soft tissue rubbing against the strip of material during mouth movements associated with talking, drinking, etc. However, this adhesion to the teeth is low enough to allow the delivery system to be easily removed by the wearer by peeling off the strip of material using one's finger or fingernail. The delivery system is easily removable from the surfaces of the teeth without the use of an instrument, a chemical solvent, or undue friction. Chemical solvents include any organic solvents commonly used in oral care products such as alcohol and other safe solvents such as water, which could be used to dilute the gelling agent. Undue friction is described as any type of rubbing with one's finger or a soft implement, such as cotton balls, swabs, or gauze pads.

A peel force of from about 1 gram to about 50 grams for a 1.5 cm strip width (approximately 17 grams/cm) is all that is required. Preferably, the peel force is from about 5 grams to about 40 grams and more preferably from about 10 grams to about 30 grams. The low peel force is desired for consumer handling purposes. The low peel force is possible because of the non-aggressive nature of a gel substance. Only when the flexural stiffness of the strip is low can the adhesion of the substance also be low. The adhesion of a stiffer strip would have to be greater in proportion to the strip stiffness in order to prevent the strip from returning to its flat condition and pulling away from the contoured surface of a plurality of teeth.

The strip of material may be formed by several of the film making processes known in the art. Preferably, a strip of material made of polyethylene is made by a blown process or a cast process. Processes, such as extrusion and other processes that do not affect the flexural rigidity of the strip of material, are also feasible. Additionally, the substance may be incorporated onto the strip during the processing of the strip. The substance may be a laminate on the strip.

Tooth Whitening Substance

The tooth whitening substance is a composition, compound, or mixture capable of influencing or effecting a desired change in appearance and/or structure of the surface it contacts. Examples of appearance and structural changes include, but are not necessarily limited to, whitening, stain bleaching, stain removal, plaque removal, and tartar removal. Preferably, the active is for the whitening of the tooth surfaces.

The tooth whitening substance may be coated on the strip of material, be applied by the user to the strip of material, or be applied by the user to their teeth and then apply the strip over the coated teeth. The amount of substance applied to the strip of material or teeth will depend upon the size and capacity of the piece of material, concentration of the active, and the desired benefit. Generally, less than about 1 gram of substance is required. Preferably, from about 0.05 grams to about 0.5 grams and more preferably from about 0.1 gram to about 0.4 grams of the substance is used. The amount of substance per square cm of material is less than about 0.2 grams/cm$^2$, preferably from about 0.005 to about 0.1 grams/cm$^2$, and more preferably from about 0.01 grams/cm$^2$ to about 0.04 grams/cm$^2$.

The substance of the present invention can be in the form of a viscous liquid, paste, gel, solution, or other suitable form that can provide sufficient adhesion. Preferably, the substance is in the form of a gel. The substance will have a viscosity of from about 200 to about 1,000,000 cps at low shear rates (less than one 1/seconds). Preferably, the viscosity is from about 100,000 to about 800,000 cps and more preferably from about 400,000 to about 600,000 cps.

Actives suitable for whitening include any material safe for use in the oral cavity which provides bleaching or stain removal. The actives suitable for whitening are selected from the group consisting of the peroxides, metal chlorites, perborates, percarbonates, peroxyacids, and combinations thereof. Suitable peroxide compounds include hydrogen peroxide, calcium peroxide, carbamide peroxide, and mixtures thereof. Most preferred is carbamide peroxide. Suitable metal chlorites include calcium chlorite, barium chlorite, magnesium chlorite, lithium chlorite, sodium chlorite, and potassium chlorite. Additional whitening actives may be hypochlorite and chlorine dioxide. The preferred chlorite is sodium chlorite.

The tooth whitening active is present in an amount of from about 0.01% to about 40%, by weight of the substance. If a peroxide compound is chosen as the active, the peroxide compound should provide an amount of hydrogen peroxide equivalent of from about 0.1% to about 20%, preferably from about 0.5% to about 10%, and most preferably from about 1% to about 7%, by weight of the substance. To deliver this amount of hydrogen peroxide equivalent, the peroxide compound, such as carbamide peroxide, is generally present in an amount of from about 0.1% to about 30% and preferably from about 3% to about 20%, by weight of the substance.

The actives are generally contained in an aqueous gel. The gel is a high viscosity matrix formed from gelling agents known in the art. These gelling agents are safe for oral use, do not readily dissolve in saliva, and do not react with or inactivate the oral care compounds incorporated into them. Generally, the gelling agent is a swellable polymer. Furthermore, the gel formed with these agents provides sufficient adhesive attachment of the film material to the targeted area of the mouth. The level of gelling agent to form the gel composition is from about 0.1% to about 15%, preferably from about 1% to about 10%, more preferably from about 2% to about 8%, and most preferably from about 4% to about 7%, by weight of the substance.

Suitable gelling agents useful in the present invention include carboxypolymethylene, carboxymethyl cellulose, carboxypropyl cellulose, poloxamer, carrageenan, Veegum, carboxyvinyl polymers, and natural gums such as gum karaya, xanthan gum, Guar gum, gum arabic, gum tragacanth, and mixtures thereof. The preferable gelling agent for use in the present invention is carboxypolymethylene, obtained from B. F. Goodrich Company under the tradename "Carbopol". Particularly preferable Carbopols include Carbopol 934, 940, 941, 956 and mixtures thereof. Particularly preferred is Carbopol 956. Carboxypolymethylene is a slightly acidic vinyl polymer with active carboxyl groups. The normal concentration of various carboxypolymethylene resins in water, according to the manufacturer, is below about 2%. However, it has been found that by preparing supersaturated carboxypolymethylene compositions having an absolute concentration in the ranges specified above, suitable high viscosity oral gel compositions may be prepared.

The concentrated carboxypolymethylene gels have a number of important characteristics in addition to high viscosity. Enough carboxypolymethylene is added to the oral gel compositions beyond that required to provide high viscosity such that a significant quantity of saliva or water is required to lower the viscosity to the point that the composition may be diluted and washed out by saliva. The concentrated carboxypolymethylene composition also has a unique tackiness or stickiness which retains and seals the strip material against the targeted oral cavity surface it is affixed to, particularly teeth. However, care should be taken to avoid too much carboxypolymethylene thereby making insertion or withdrawal of the strip material difficult.

Water is also present in the gel compositions disclosed herein. The water, employed in the present invention should, preferably, be deionized and free of organic impurities. Water comprises from about 0.1% to 95%, preferably from about 5% to about 90%, and most preferably from about 10% to about 80%, by weight of the substance. This amount of water includes the free water that is added plus that amount that is introduced with other materials.

A pH adjusting agent may also be added to optimize the storage stability of the gel and to make the substance safe for oral tissues. These pH adjusting agents, or buffers, can be any material which is suitable to adjust the pH of the substance. Suitable materials include sodium bicarbonate, sodium phosphate, sodium hydroxide, ammonium hydroxide, sodium stannate, triethanolamine, citric acid, hydrochloric acid, sodium citrate, and combinations thereof. The pH adjusting agents are added in sufficient amounts so as to adjust the pH of the gel composition to about 4.5 to about 11, preferably from about 5 to about 8.5, and more preferably from about 5.5 to about 7. pH adjusting agents are generally present in an amount of from about 0.01% to about 15% and preferably from about 0.05% to about 5%, by weight of the substance.

While the gel described above provides sufficient adhesiveness, additional gelling agents may also be included in the formula to help the active ingredients adhere to the tissues of the oral cavity. Suitable agents include both polymers with limited water solubility as well as polymers lacking water solubility. These polymers deposit a thin film on both the oral cavity's soft and hard tissues when saliva combines with the instant composition. Suitable limited water solubility adhesives include: hydroxy ethyl or propyl cellulose. Adhesives lacking water solubility include: ethyl cellulose and polyox resins. Another possible adhesive suitable for use in the instant composition is polyvinylpyrrolidone with a molecular weight of about 50,000 to about 300,000. Still another possible adhesive suitable for use in the instant composition is a combination of Gantrez and the semisynthetic, water-soluble polymer carboxymethyl cellulose.

An additional carrier material may also be added to the substance. Carrier materials can be humectants. Suitable humectants include glycerin, sorbitol, polyethylene glycol, propylene glycol, and other edible polyhydric alcohols. Humectants are generally present in an amount of from about 10% to about 95%, preferably from about 20% to about 80%, and more preferably from about 50% to about 70%, by weight of the substance. In addition to the above materials of the gel of the present invention, a number of other components can also be added to the substance. Additional components include, but are not limited to, flavoring agents, sweetening agents, xylitol, opacifiers, coloring agents, and chelants such as ethylenediaminetetraacetic acid. These additional ingredients can also be used in place of the compounds disclosed above.

Release Liner

The release liner may be formed from any material which exhibits less affinity for substance than substance exhibits for itself and for the strip of material. The release liner preferably comprises a rigid sheet of material such as polyethylene, paper, polyester, or other material which is then coated with a non-stick type material. The release liner material may be coated with wax, silicone, polyester such as Teflon®, fluoropolymers, or other non-stick type materials. A preferred release liner is Scotchpak®, produced by 3M. The release liner may be cut to substantially the same size and shape as the strip of material or the release liner may be cut larger than the strip of material to provide a readily accessible means for separating the material from the strip. The release liner may be formed from a brittle material which cracks when the strip is flexed or from multiple pieces of material or a scored piece of material. Alternatively, the release liner may be in two overlapping pieces such as a typical adhesive strip bandage type design. A further description of materials suitable as release agents is found in Kirk-Othmer Encyclopedia of Chemical Technology, Fourth Edition, Volume 21, pp. 207–218, incorporated herein by reference.

EXAMPLES

The strip of material is preferably a 0.009 mm thick piece of polyethylene film. The film preferably has an array of shallow pockets, typically 0.4 mm across and 0.1 mm deep. The strip of material has a flexural stiffness of about 0.6 grams/cm as measured on a Handle-O-Meter, model #211-300, available from Thwing-Albert Instrument Co. of Philadelphia, Pa., as per test method ASTM D2923-95.

An example of a tooth whitener is a gel described as follows: Combine 70% glycerin, 5% carboxypolymethylene, 10% carbamide peroxide, and 15% water adjusted to pH 6.5 with sodium hydroxide. Mix until homogeneous.

Additional examples of alternative tooth whitening gel are described as follows: Combine 8% carboxypolymethylene in approximately 84% water, add 4% sodium hydroxide and enough sodium bicarbonate to bring the pH to about 10. Dissolve in 3.75% sodium chlorite and mix until homogeneous.

Combine 60% glycerin, 4.5% carboxypolymethylene, and 5% hydrogen peroxide. Add sodium hydroxide (50% solution) until the pH is adjusted as desired and then add the remainder as water. Mix until homogeneous.

Combine 56% glycerin, 6% carboxypolymethylene, 10% carbamide peroxide, and 24% water. Add 4% sodium hydroxide (50% solution) to adjust the pH. Mix until homogeneous.

Combine 68% glycerin, 6% carboxypolymethylene, 22% carbamide peroxide, and 4% sodium hydroxide (50% solution). Mix until homogeneous.

Combine 25% glycerin, 69.7% water, 2% xanthan gum, 3% carboxymethylcellulose, and 0.3% carbamide peroxide. Mix until homogeneous.

Combine 24% poloxamer, 20% glycerin, 46% polyethylene glycol, and 10% carbamide peroxide. Mix until homogeneous.

Commercial tooth whiteners, such as Opalescence and Nu-Pro Gold, are also operable with the delivery system of the present invention.

Method of Use

In practicing the present invention, a strip of material is applied by the user to the teeth. The side of the material facing the teeth is coated with a tooth whitening substance which is preferably in a viscous state to provide not only the active but also tackiness between the tooth surfaces and the strip of material to hold the strip in place for an extended period of time. Alternatively, the user may apply a tooth whitening substance to the teeth or to the strip before applying the strip to the teeth. The strip of material readily conforms to the teeth by lightly pressing it against the teeth and/or by the wearer gently sucking through the gaps between the teeth. The strip of material is easily removed by the wearer by peeling it off. Preferably, each successive treatment will use a fresh strip of material.

The tooth surface is not required to be prepared before the delivery system is applied. For example, the wearer may or may not choose to brush his teeth or rinse his mouth before applying the delivery system. The surfaces of the teeth are not required to be dried or to be excessively wet with saliva or water before the strip of material is applied.

Preferably, the strip of material and substances are substantially transparent so as to be almost unnoticeable when worn. Thinness of the delivery system enables the higher temperature inside of the wearer's mouth to conduct heat through the strip of material to the normally cooler teeth in order to accelerate the rate of diffusion of the active material into the surfaces of the teeth.

Preferably, the wearer applies the delivery system of the present to the teeth continuously for about 5 minutes to about 120 minutes a day, preferably from about 30 minutes to about 60 minutes. Generally, this is done once a day for about 7 to 28 days. The amount of time and the number of days are dependent upon several factors, including the amount of bleaching desired, the wearer's teeth, and if initial or maintenance bleaching is desired. The bleaching is done to achieve a whitening benefit of 1–4 shade guide improvement as measured by VITA LUMIN® Vacuum Farbskala Shade Guides, a product of VITA Zahnfabrik, of BadSackingen, Germany.

When the wearer removes the strip of material from the tooth, there may be a residue of substance remaining on the surface. This residual will not be great, as the tooth whitening substance has affinity for both the film and for itself. If residual substance remains, it may be easily removed by brushing or rinsing.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

What is claimed is:

1. A method of bleaching a plurality of adjacent teeth, the teeth having facial and lingual surfaces, comprising:
    applying a tooth bleaching delivery system to a plurality of adjacent teeth, wherein the tooth bleaching delivery system comprises a strip of material and a tooth bleaching composition having a peroxide active and wherein the strip of material comprises a plurality of layers and one of the layers is a non-woven material, wherein applying the tooth bleaching system comprises:
    a) applying a first portion of the strip of material and tooth bleaching composition to the facial surfaces of the plurality of adjacent teeth so that the tooth bleaching composition contacts the facial surfaces of the plurality of adjacent teeth;
    b) folding a second portion of the strip of material and tooth bleaching composition about the incisal edges of the plurality of adjacent teeth;
    c) applying the second portion of the strip and tooth bleaching composition to at least a portion of the lingual surfaces of one or more of the plurality of adjacent teeth, wherein the tooth bleaching composition is adhesive during use and wherein the tooth bleaching delivery system is applied to the facial and lingual surfaces of the plurality of adjacent teeth for a sufficient period of time for the peroxide active to act upon the facial surfaces of the plurality of adjacent teeth; and
    wherein the tooth bleaching delivery system is applied for a period of time between about 5 minutes and about 120 minutes.

2. The method of claim 1, wherein said peroxide is carbamide peroxide.

3. The method of claim 2, wherein the tooth bleaching composition further comprises glycerin, carboxypolymethylene, triethanolamine, and a flavoring agent.

4. The method of claim 1, wherein said tooth whitening delivery system is applied for a period of time between about 30 minutes and about 60 minutes.

5. The method of claim 1, further comprising repeating 1(a) to 1(c) once a day for about 7 to about 28 days.

6. The method of claim 1, wherein said strip of material has two sides that are arched.

7. The method of claim 1, wherein said strip of material has two sides that are stair stepped, and wherein said stairstepped sides fold about the incisal edge of the plurality of adjacent teeth.

8. The method of claim 1, wherein the tooth bleaching composition comprises a mixture of polymers.

9. The method of claim 8, wherein said mixture of polymers comprises polyvinylpyrrolidone.

10. The method of claim 9, wherein said tooth bleaching mixture further comprises polyethylene glycol.

11. The method of claim 10, wherein said tooth bleaching mixture further comprises water and wherein said peroxide is hydrogen peroxide.

12. The method of claim 1, wherein said tooth bleaching composition comprises a poloxamer.

13. The method of claim 1, wherein said tooth bleaching delivery system is applied to the teeth once per day.

14. The method of claim 1, wherein a fresh strip of material is used for each application of said tooth bleaching substance to said surfaces of said teeth.

15. The method of claim 1, wherein said strip of material is removed from the surfaces of said teeth by peeling off said strip of material.

16. The method of claim 1, further comprising repeating 1(a) to 1(c) until a whitening benefit of a 1–4 shade guide improvement is achieved.

17. A method of bleaching a plurality of adjacent teeth, the teeth having facial and lingual surfaces, comprising:
applying a tooth bleaching delivery system to a plurality of adjacent teeth, wherein the tooth bleaching delivery system comprises a strip of material and a tooth bleaching composition having a peroxide active, wherein applying the tooth bleaching system comprises:
a) applying a first portion of the strip of material and tooth bleaching composition to the facial surfaces of the plurality of adjacent teeth so that the tooth bleaching composition contacts the facial surfaces of the plurality of adjacent teeth;
b) folding a second portion of the strip of material and tooth bleaching composition about the incisal edges of the plurality of adjacent teeth;
c) applying the second portion of the strip and tooth bleaching composition to at least a portion of the lingual surfaces of one or more of the plurality of adjacent teeth, wherein the tooth bleaching composition is adhesive during use and wherein the tooth bleaching delivery system is applied to the facial and lingual surfaces of the plurality of adjacent teeth for a sufficient period of time for the peroxide active to act upon the facial surfaces of the plurality of adjacent teeth; and wherein 12(a) to 12(c) are repeated for about 7 days.

18. The method of claim 17, wherein said peroxide is carbamide peroxide.

19. The method of claim 18, wherein the tooth bleaching composition further comprises glycerin, carboxypolymethylene, triethanolamine, and a flavoring agent.

20. The method of claim 17, wherein said tooth whitening delivery system is applied for a period of time between about 5 minutes and about 120 minutes.

21. The method of claim 17, wherein said strip of material has two sides that are arched.

22. The method of claim 17, wherein said strip of material has two sides that are stair-stepped, and wherein said stairstepped sides fold about the incisal edge of the plurality of adjacent teeth.

23. The method of claim 17, wherein the tooth bleaching composition comprises a mixture of polymers.

24. The method of claim 23, wherein said mixture of polymers comprises polyvinylpyrrolidone.

25. The method of claim 24, wherein said tooth bleaching mixture further comprises polyethylene glycol.

26. The method of claim 25, wherein said tooth bleaching mixture further comprises water and wherein said peroxide is hydrogen peroxide.

27. The method of claim 17, wherein said tooth bleaching composition comprises a poloxamer.

28. The method of claim 17, wherein said tooth bleaching delivery system is applied to the teeth once per day.

29. The method of claim 17, wherein a fresh strip of material is used for each application of said tooth bleaching substance to said surfaces of said teeth.

30. The method of claim 17, wherein said strip of material is removed from the surfaces of said teeth by peeling off said strip of material.

31. The method of claim 17, further comprising repeating 12(a) to 12(c) until a whitening benefit of a 1–4 shade guide improvement is achieved.

* * * * *

UNITED STATES PATENT AND TRADEMARK OFFICE
CERTIFICATE OF CORRECTION

| | | |
|---|---|---|
| PATENT NO. | : 7,122,199 B2 | Page 1 of 1 |
| APPLICATION NO. | : 11/099738 | |
| DATED | : October 17, 2006 | |
| INVENTOR(S) | : Paul Albert Sagel et al. | |

It is certified that error appears in the above-identified patent and that said Letters Patent is hereby corrected as shown below:

Column 13
 Claim 17, Line 31 – delete "12(a) to 12(c)" and insert --17(a) to 17(c)--

Column 14

Claim 31, Line 34 – delete "12(a) to 12(c)" and insert --17(a) to 17(c)--

Signed and Sealed this

Ninth Day of January, 2007

JON W. DUDAS
*Director of the United States Patent and Trademark Office*